United States Patent [19]

Byers et al.

[11] Patent Number: 4,837,358

[45] Date of Patent: Jun. 6, 1989

[54] PREPARATION OF 9-ALKENYL ESTER COMPOUNDS

[75] Inventors: Jim D. Byers; Charles A. Drake, both of Bartlesville, Okla.

[73] Assignee: Phillips Petroleum Company, Bartlesville, Okla.

[21] Appl. No.: 833,301

[22] Filed: Feb. 26, 1986

[51] Int. Cl.[4] ............................................ C07C 67/317
[52] U.S. Cl. .............................. 560/261; 260/665 G; 260/665 R; 556/170; 556/181; 568/851
[58] Field of Search ................ 560/261; 556/170, 181, 556/52, 51; 568/1, 6, 7, 851; 260/665 G, 665 R

[56] References Cited

U.S. PATENT DOCUMENTS

| | | | |
|---|---|---|---|
| 3,845,108 | 10/1974 | Roelofs et al. | 560/261 |
| 3,980,771 | 9/1976 | Meijer et al. | 424/84 |
| 3,985,813 | 10/1976 | Labovitz et al. | 260/632 Y |
| 4,059,689 | 11/1977 | Struble et al. | 424/84 |
| 4,243,660 | 1/1981 | Szantay et al. | 424/84 |
| 4,364,931 | 12/1982 | Szantay et al. | 424/84 |

OTHER PUBLICATIONS

Dolzine, T. W. et al, Journal of Organometallic Chemistry 78 (1974) pp. 165–176.
Hendrick, Clive A, The Synthesis of Insect Sex Pheromones Tetrahedron, vol. 33, pp. 1845–1889 (1977).
Rossi, Renzo, Insect Pheromones; I. Synthesis of Achiral Components of Insect Pheromones, Synthesis, pp. 817–836, (1977).

*Primary Examiner*—Werren B. Lone
*Attorney, Agent, or Firm*—Hal B. Woodrow

[57] ABSTRACT

Process for the production of 9-alkenyl acetates is provided. The process comprises first disproportionating cyclooctene with an α-olefin to give a 1,9-alkadiene. The alkadiene is metallated to form a 1-metallo-9-alkene, which is then contacted with oxygen to produce a 9-alkenyl-1-oxymetallo compound, which is optionally hydrolyzed to the corresponding alcohol, with the alcohol being esterified to the desired 9-alkenyl ester or the 9-alkenyl-1-oxymetallo compound can be directly esterified, to produce the desired 9-alkenyl esters.

21 Claims, No Drawings

PREPARATION OF 9-ALKENYL ESTER COMPOUNDS

This invention relates to the preparation of 9-alkenyl esters.

BACKGROUND

9-Alkenyl esters, such as 9-dodecadienyl acetate, 9-tetradecenyl formate, 9-tetradecenyl acetate, 9-hexadecenyl acetate, and the like, are known pheromones or pheromone mimics for several insect species. In order to make these compounds widely available for use in insect control, economic large scale synthetic conversion processes for their preparation must be developed. While several synthetic routes for the preparation of various 9-alkenyl ester compounds have been disclosed in the prior art, the known synthetic routes are usually specific for the preparation of only one target pheromone or pheromone mimic. In addition, known synthetic routes suffer from the disadvantages of requiring multiple reaction steps with consequent low overall product yield, consumption of large quantities of reagents which do not contribute to the final product structure, and the like.

For example, in Tetrahedron, Volume 33, 1845 at 1846 (Pergamon Press 1977), Henrick describes a multi-step synthesis of 9-dodecadienyl acetate which involves: (1) the bromination of 1,8-octanediol with hydrobromic acid to give 8-bromo-1-octanol, (2) etherification of 8-bromo-1-octanol with dihydropyran, (3) alkylation of the tetrahydropyranyl ether with the lithium salt of 1-butyne while concurrently reducing the triple bond with sodium in liquid ammonia, and finally (4) the tetrahydropyranyl ether is converted to the desired acetate with acetyl chloride and glacial acetic acid. Variations of this synthetic scheme which require an even greater number of reaction steps are also disclosed by Henrick.

In Synthesis, 1977, pages 817–836, Rossi reviews synthetic methods employed for the preparation of pheromones. Pheromones having 9-Z-configuration are prepared by reaction of a solution of an appropriately selected carbonyl compound in hexamethylphosphoric triamide with an ylid obtained by reacting the corresponding phosphonium salt with the products of the reaction between potassium metal and hexamethylphosphoric triamide. While high stereoisomeric purity products are obtained, reaction yields are low and the reagents employed are expensive.

In summary, due to the large number of reaction steps required, the relative inavailability or high expense of many needed reagents, and the step wise fashion in which the desired carbon backbone is constructed, known synthetic routes for the production of 9-alkenyl esters are not amenable to being carried out economically on a large scale.

OBJECTS OF THE INVENTION

An object of the present invention, therefore, is an efficient and economic process for the synthesis of 9-alkenyl esters.

This and other objects of the invention will become apparent from further study of the disclosure and claims herein provided.

STATEMENT OF THE INVENTION

In accordance with the present invention, we have discovered that disproportionation of cyclooctene and an α-olefin in the presence of a disproportionation catalyst produces a 1,9-alkadiene which can be metallated to produce a 1-metallo-9-alkene which is then oxidized and esterified to produce the desired 9-alkenyl ester. The product 9-alkenyl esters are useful, for example, as insect sex attractants.

DETAILED DESCRIPTION OF THE INVENTION

In accordance with the present invention, a process for the preparation of 9-alkenyl esters is provided which comprises:

(a) disproportionating cyclooctene and an α-olefin in the presence of a disproportionation catalyst under disproportionation conditions suitable to give a 1,9-alkadiene, (b) metallating the resulting 1,9-alkadiene with a metallating agent under conditions suitable to give a 1-metallo-9-alkene, (c) contacting the 1-metallo-9-alkene obtained from step (b) with oxygen under conditions suitable to give a 9-alkenyl-1-oxymetallo compound, and (d) esterifying the 9-alkenyl-1-oxymetallo compound to form the desired 9-alkenyl ester.

The starting materials employed in the practice of the present invention are cyclooctene and an appropriate α-olefin. Since all the carbon atoms of both the cyclooctene and the α-olefin will be retained in the ultimate ester product, the appropriate α-olefin is selected so as to define the total chain length of the product 9-alkenyl ester. Thus, if a 9-dodecenyl ester is desired, 1-butene is the appropriate α-olefin to employ, while if a 9-tetradecenyl ester is desired, 1-hexene is the appropriate olefin to employ. The synthetic procedure of the present invention is operable employing α-olefins having from about 3 up to about 12 carbon atoms. Since the most common currently known pheromones have 12 or 14 carbon atoms, 1-butene and 1-hexene are the presently preferred α-olefins. These α-olefins are also preferred because of their relative low cost and ready availability.

The disproportionation of cyclooctene and an α-olefin can be carried out in a variety of ways as recognized by those of skill in the art. Thus, any suitable ratio of cyclooctene/α-olefin can be employed in the presence of a wide variety of disproportionation catalysts. For most efficient utilization of the reaction components, a molar ratio of about 1:1 is preferred, although good conversions are obtained with cyclooctene/α-olefin ratios ranging from about 5:1 to about 1:5.

A wide variety of heterogeneous and homogeneous disproportionation catalysts are known in the art and are capable of promoting the disproportionation of cyclooctene plus α-olefin to produce 1,9-alkadienes. Our invention is not limited to the use of a specific disproportionation catalyst, but any catalyst suitable for disproportionation of cyclooctene plus α-olefins can be utilized.

Suitable heterogeneous catalysts useful in the practice of the present invention include:

(1) silica or thoria promoted by an oxide or compound convertible to an oxide by calcination, or sulfide of tungsten or molybdenum; or by an oxide or compound convertible to an oxide by calcination of rhenium or tellurium;

(2) alumina promoted with an oxide or compound convertible to an oxide by calcination of molybdenum, tungsten, or rhenium; a sulfide of tungsten or molybdenum; or an alkali metal salt, ammonium salt, alkaline earth metal salt, or bismuth salt of phosphomolybdic acid;

(3) one or more of the group aluminum phosphate, zirconium phosphate, calcium phosphate, magnesium phosphate, or titanium phosphate promoted by one or more of a sulfide of molybdenum or tungsten, or an oxide or compound convertible to an oxide by calcination of molybdenum, tungsten or rhenium or magnesium tungstate or beryllium phosphotungstate;

(4) silica, alumina, aluminum phosphate, zirconium phosphate, calcium phosphate, magnesium phosphate, or titanium phosphate promoted by a hexacarbonyl of molybdenum or tungsten; and (5) (a) molybdenum oxide or tungsten oxide associated with suitable support material and (b) at least one organoaluminum compound, optionally, treated with nitric oxide or nitrosyl halides.

The catalysts of (1) can be prepared and activated by conventional techniques such as by combining a catalyst grade silica with suitable tungsten, molybdenum, rhenium or tellarium compounds by a conventional method such as, for example, impregnation, dry mixing, or co-precipitation. Suitable tungsten and molybdenum compounds include tungsten oxide and molybdenum oxide and compounds convertible to these oxides. The supported oxides are activated by calcining in air and the supported sulfide are activated by heating in an inert atmosphere.

The catalysts of (2) can be prepared and activated by conventional techniques such as by combining catalyst grade alumina with an oxide or a compound convertible to an oxide by calcination of molybdenum, tungsten or rhenium and calcining the resulting mixture after removal of any solvent used in the impregnation. The sulfides of tungsten or molybdenum or the salts of phosphomolybdic acid can be utilized to impregnate a catalyst grade alumina by solution in a proper solvent after which the solvent is evaporated and the resulting mixture dried to prepare the catalyst.

The catalyst compositions of (3) can be prepared and activated by conventional techniques. For example, molybdenum oxide can be co-precipitated with aluminum phosphate followed by calcination in air to produce an activated catalyst. Alternatively, the support material can be impregnated with a compound of the promoter convertible to the oxide, such as ammonium tungstate, followed by calcination in air. In the preparation of a sulfide-containing catalyst, a sulfide of the promoter can be ball-milled with a support, such as zirconium phosphate, followed by heating in an inert atmosphere such as nitrogen. Magnesium tungstate and beryllium phosphotungstate can be dry mixed with titanium phosphate, for example, and activated by calcination in air at elevated temperatures.

The catalyst compositions of (4) can be prepared and activated by impregnating a previously calcined support material such as calcium phosphate with a solution of the hexacarbonyl of the promoter in an organic solvent such as benzene, followed by drying in a vacuum or in an inert atmosphere at about 10° to 375° C. (50° to 700° F.).

The (a) components of the catalyst system (5) are active by themselves for the disproportionation of olefins. However, the activity of this system is exhibited at relatively high temperatures which are generally above 150° C. for optimum operation.

Suitable support materials which are combined with the oxides of molybdenum and tungsten to form the (a) component of the catalyst system (5) include alumina, silica, silica-alumina, magnesia-titania, thoria, aluminum phosphate, zirconium phosphate, titanium phosphate, calcium phosphate, magnesium phosphate, and mixtures thereof.

Preferred combinations of the above support materials with the oxides of molybdenum and tungsten promoter materials include (i) silica or thoria promoted by the oxide or a compound convertible to an oxide by calcination of tungsten or molybdenum; (ii) alumina promoted by an oxide, or compound convertible to an oxide by calcination of molybdenum or tungsten; and (iii) one or more of the group aluminum phosphate, zirconium phosphate, calcium phosphate, magnesium phosphate, or titanium phosphate promoted by one or more of an oxide of molybdenum or tungsten, or by a compound of molybdenum or tungsten convertible to an oxide by calcination.

The combinations of (i), (ii), or (iii) can be prepared and activated by suitable methods such as, for example, impregnation, dry mixing, or co-precipitation.

When the promoter is tungsten oxide, the preferred support material is silica or silica-containing materials. The preferred support materials for molybdenum oxide are alumina, alumina-containing materials, silica or silica-containing materials. In general the (a) component of the catalyst system (5) will contain about 0.1 to about 30, preferably from about 1 to about 15 weight percent of the molybdenum or tungsten oxide. In addition, it is sometimes desirable that this component of the catalyst system of the invention contain relatively small amounts, from about 0.005 to about 5, preferably 0.1 to 2, weight percent of an inorganic base material. Suitable inorganic base materials include alkali metal and alkaline earth metal hydroxides and carbonates, sodium hydroxide, potassium hydroxide, sodium carbonate and potassium carbonate being preferred.

The solid (a) component of the system (5) catalysts can be in any conventional catalytic shape or size, depending upon the type of conversion in which it is to be utilized. For example, in fixed bed catalyst systems, the solid composite can be in the form of spheres, pellets, extrudates, agglomerates and the like. In slurry catalyst systems, the solid can be in the form of relatively small particles or in the form of a powder.

To be effective in the present catalyst system, the above-described (a) component of the catalyst system (5) is activated at elevated temperatures, generally in flowing air. The activation of the catalysts is accomplished at a temperature ranging from about 260° to 870° C. (500° to 1600° F.) for a period of several seconds to several hours. When the (a) component of the catalyst system is tungsten oxide on silica, a convenient and economical activation treatment is in the temperature range of about 480° to 650° C. (900° to 1200° F.) for a period of 15 minutes to 5 hours. When the (a) component of the catalyst system (5) is a supported molybdenum oxide, a convenient and economical treatment is in the temperature range of about 480° to 760° C. (900° to 1400° F.) for 0.5 to 20 hours or longer. In some cases the activation using an oxygen-containing gas can be followed by treatment, also at elevated temperatures, with other treating gases such as carbon monoxide, hydrogen and the like.

The organoaluminum compounds which are applicable for use as the (b) component in catalyst (5) have the formula $R''_a AlX_b$ where $R''$ is a saturated aliphatic or aromatic hydrocarbon having up to about 20 carbon atoms. X is chlorine, bromine, iodine, or fluorine, a is an integer of at least 1, b can be 0, 1 or 2, and the total of a and b is 3, thus a can be 1, 2 or 3. Such aluminum compounds are well known in the art and are generally commercially available.

Some examples of suitable organoaluminum compounds halide are methylaluminum dichloride, dimethylaluminum fluoride, methylaluminum sesquichloride, trimethylaluminum, ethylaluminum dichloride, ethylaluminum sesquichloride, di(2-ethylhexyl)aluminum bromide, triisobutylaluminum, phenylaluminum dichloride, (di(3-methylpentyl)-aluminum bromide, cyclohexylaluminum dichloride, benzylaluminum diodide, dieicosylaluminum bromide, and the like, and mixtures thereof. The preferred (b) components are the organoaluminum halides, especially those wherein the hydrocarbon portion is an alkyl radical of 1 to 5 carbon atoms. Particularly good results are obtained with ethylaluminum dichloride, diethylaluminum chloride, and mixtures such as ethylaluminum sesquichloride and methylaluminum sesquichloride.

The molar proportion of the organoaluminum (b) component to the solid (a) component to form the catalyst system (5) useful in the practice of the present invention will generally be in the range of from about 0.005:1 to 20:1, preferably from about 0.01:1 to 10:1 moles of the (b) component per mole of the molybdenum or tungsten oxide contained in the (a) component.

It is sometimes preferred that the supported tungsten or molybdenum component, before contacting the organoaluminum compound, be treated either with nitric oxide or with a nitrosyl halide. Such treatment can take place at a temperature preferably in the range of about 0° to 130° C., more preferably about 20° to 60° C., for a time in the range of from a few seconds up to about 24 hours, and preferably in the presence of a diluent in which the nitric oxide or nitrosyl halide is at least partially soluble. After such treatment, the diluent and excess nitric oxide or nitrosyl halide can be removed from the solid catalyst by decantation, evaporation, and similar techniques. This treatment, however, should be carried out in the substantial absence of moisture, preferably in an inert atmosphere, to preserve the effects of the previous activation by calcination.

The catalyst system (5) useful in the practice of the present invention is prepared simply by combining the solid (a) component with the organoaluminum (b) component under conditions of time and temperature which permit the catalytically active catalyst composition to be formed. The combination occurs very readily, and, in general, the components can be mixed at any convenient temperature, room temperature frequently being satisfactory, in the presence of a diluent in which the organoaluminum compound is at least partially soluble. Any convenient diluent such as, for example, benzene, cyclohexane, toluene, chlorobenzene, methylene chloride, ethylene chloride, and the like, can be used for this purpose. Halogenated diluents are generally preferred. The mixing of these two catalyst components is carried out in the substantial absence of air or moisture, generally in an inert atmosphere. After the catalytic reaction mixture is formed, it need not be isolated but can be added directly to the olefin reaction zone as a suspension in its preparation medium. If desired, the catalyst components can be separately added, in any order, to the reaction zone either in the presence or absence of the feed olefin.

Alternatively, the system (5) catalysts useful in the practice of the invention can be separated from the preparation medium and the dissolved organoaluminum compound therein by decantation, and, after additional washing and/or drying if desired, can be added to the reaction zone as a solid rather than as a suspension.

The operating temperature for the process of this invention when using heterogeneous catalysts of (1) is in the range of about 90° to 600° C. (200° to 1100° F.). The process of this invention when using the catalysts of (2) will be operated at a temperature in the range of about 65° to 260° C. (150° to 500° F.). The process using the catalysts of (3) will be carried out in a temperature range of about 315° to 650° C. (600° to 1200° F.). The process using the catalysts of (4) will be carried out in a temperature range of about −20° to 315° C. (0° to 600° F.). In the process of the invention, pressures are not important but will be generally in the range of about 0 to 2,000 psig.

According to the process of the invention employing catalyst system (5), the mixture of olefins to be converted, i.e., cyclooctene and an α-olefin, is contracted with the catalyst under conditions suitable to obtain the desired reaction, for example, at a temperature in the range of about 0° to 150° C. and at any convenient pressure. Preferably, the temperature is in the range of about 15° C. to 50° C. wherein good results are obtained economically. Excellent results are obtained by contacting the olefin feed material with the catalyst at room temperature. The conversion can be carried out in the presence of any inert diluent such as that used for the catalyst preparation, if desired. Diluents are not essential but are sometimes preferred and such diluents can include saturated aliphatics and aromatics such as cyclohexane, xylene, isooctane, and the like, and halogenated derivatives thereof. The time of contact will depend upon the desired degree of conversion and the catalysts utilized, but will, generally, be in the range of from 0.1 minute to 24 hours, preferably 5-120 minutes. The proportion of catalyst composition to olefin feed in the reaction zone will generally be in the range of from about 0.001 to 100 millimoles of the molybdenum or tungsten oxide contained in the solid catalyst, for each mole of olefin in the reacting zone.

The oxide-promoted catalysts useful in the practice of this invention are activated by heat treatment at temperatures of from 315° to 815° C. (600° to 150020 F.) for a period of about 1 second to 25 hours or more, shorter times being used with higher temperatures and longer times with the lower temperatures. A convenient and economical treatment is obtained by subjecting the catalyst to contact with a stream of air at a temperature in the range of about 480° to 650° C. (900° to 1200° F.) for from about 15 minutes to 5 hours. Other gases, which do not poison the catalyst, for example, nitrogen, can also be sometimes used either as a substitute for the air treatment, or as a subsequent flush. Air is usually preferred for activation, since it is readily available.

Any conventional contacting technique can be used for the olefin disproportionation employing the heterogeneous catalysts disclosed herein, and batchwise or continuous operation can be utilized. After the reaction period, the products can be separated and/or isolated by any suitable means such as by fractionation, crystallization, adsorption, and the like. Unconverted feed materials or products not in the desired molecular weight range can be recycled to the conversion zone. After separation of the products, the solid catalyst can be recycled to the reaction zone either with or without the addition of a fortifying amount of organoaluminum halide.

The heterogeneous catalysts employed in the practice of the invention can be further treated with modifying amounts of compounds of alkali metals or alkaline earth metals.

The catalyst supports and promoting agents employed can contain other materials which do not have a deleterious effect on the desired reaction or promote the formation of undesired by-products.

Suitable homogeneous catalysts employed in the practice of the present invention include:

(a) the coordination compounds of molybdenum or tungsten as disclosed in U.S. Pat. No. 3,778,385, which disclosure is hereby incorporated by reference;

(b) the coordination compounds of molybdenum or tungsten complexed with NO, together with an organoaluminum adjuvant, as disclosed in U.S. Pat. No. 4,010,217, which disclosure is hereby incorporated by reference;

(c) the neutral carbene complex catalysts disclosed in U.S. Pat. No. 4,247,417, which disclosure is hereby incorporated by reference;

(d) the neutral carbene complex catalysts disclosed in U.S. Pat. No. 4,248,738, which disclosure is hereby incorporated by reference;

(e) the neutral carbene complex catalysts disclosed in U.S. Pat. No. 4,269,780, which disclosure is hereby incorporated by reference;

(f) other homogeneous catalysts known by those of skill in the art such as, for example, $WCl_6 + SnMe_4$; $W(CH_2C_6H_5)_3Cl + AlCl_3$; $WOCl_4 + R_4Sn$; and the like.

It is also recognized by those of skill in the art that the homogeneous catalysts detailed herein can be deposited on solid support and employed as solid phase catalysts.

The metallation of the 1,9-alkadienes to form 1-metallo-9-alkenes can be carried out employing a variety of metallating agents. Any metallating agent capable of selective reaction with the terminal double bond of the 1,9-alkadiene starting material is suitable. Examples of suitable metallating agents include organoboranes, organoaluminum compounds, organomagnesium compounds, organozirconium compounds and the like.

Organoboranes contemplated to be within the scope of the present invention can be described as "hindered" organoborane compounds and can be represented by the following formula:

$R_2BH$ wherein each R is independently a $C_1$ to $C_{10}$ carbon radical wherein at least one R group is a secondary or tertiary alkyl group and each R group can be connected to the other as part of a ring structure. Exemplary compounds which satisfy the above formula include disiamylborane (i.e., bis-(3-methyl-2-butyl)borane), 9-borabicyclo [3.3.1]nonane (9-BBN), dithexylborane, thexylcyclopentylborane, thexylcyclohexylborane, and the like.

The hydroboration reaction is generally carried out in the presence of a suitable solvent such as, for example, tetrahydrofuran (THF). A roughly equimolar mixture of diene and organoborane reagent are combined. Preferably, a slight excess of diene is employed to minimize the likelihood of hydroboration occurring on the internal double bonds of the starting material diene. Typically, the hydroboration reaction should be carried out in an inert atmosphere; i.e. moisture and oxygen should be excluded from the reaction mixture. Reaction conditions employed are broadly 0°–100° C. for a few minutes up to several hours. Preferably, the hydroboration is carried out at about 20°–80° C. for 15 minutes up to about 2 hours. Reaction is generally carried out at about atmospheric pressure, although higher and lower pressures are acceptable.

Organoaluminum compounds contemplated to be within the scope of the present invention can be described by reference to the formula:

$AlR'_3$ wherein each R' is independently H, or a $C_1$ to $C_{20}$ carbon radical. Examples of suitable organoaluminum compounds include triisobutyl-aluminum, diisobutylaluminum hydride, diisopropylaluminum hydride and the like.

The organoaluminum compounds are presently preferred because of their relative low cost, high reaction yields, etc.

Organozirconium compounds contemplated to be within the scope of the present invention can be described by the formula:

$(Ar)_2Zr(X)H$ wherein Ar is an aromatic ligand having 5–10 carbon atoms, such as phenyl, cyclopentadienyl, methylcyclopentadienyl, and the like, and X is a halogen. Examples of suitable organozirconium compounds include biscyclopentadienylzirconuim chlorohydride, biscyclopentadienylzirconium bromohydride, bispentamethylcyclopentadienylzirconium chlorohydride, bismethylcyclopentadienylzirconium chlorohydride, bis-dimethylcyclopentadienylzirconium chlorohydride, and the like.

Organomagnesium compounds contemplated to be within the scope of the present invention can be described by reference to the following formulae:

$R''MgX$, and $R''_2Mg$ wherein R'' has at least one $\beta$-hydrogen, and therefore is a $C_2$ to $C_{10}$ carbon radical and X is Cl, Br or I. Exemplary compounds which satisfy the above formulae include various Grignard reagents, such as, for example, ethylmagnesium bromide, isopropylmagnesium bromide, butyl-magnesium bromide, and the like. Additional examples include dialkyl-magnesium compounds such as, for example, diethylmagnesium, diisopropylmagnesium and the like.

Metallation with organomagnesium compounds is generally carried out in the presence of at least one transition metal activating agent. Suitable transition metal activating agents include nickel, titanium, vanadium and zirconium compounds. Exemplary titanium activating agents include a titanocene dichloride such as, for example, biscyclopentadienyl titanium dichloride, or alternatively, titanium tetrachloride. The molar ratio of organomagnesium compound to diene should be at least about 1:1 with the presence of a small excess of the organomagnesium compound acceptable, i.e., up to about to a 1.5 to 1 molar ratio. The molar ratio of diene to transition metal reagent is generally in the range of about 1–500:1 and preferably about 50–100:1.

Metallation with organomagnesium compounds is generally carried out at atmospheric pressure, although higher and lower pressures are operable. Preferably, atmospheric pressure or slightly reduced pressures will be employed since pressures in excess of atmospheric will tend to retard the reaction rate. Reaction temperatures of about $-20°$ to about $100°$ C. for at least one minute up to about 24 hours are suitable. Preferably, reaction temperature will be maintained between about $0°$ and $60°$ C., for about 15 minutes to about 6 hours.

The 1-metallo-9-alkenes prepared as described above have the empirical formula $C_nH_{2n-1}M$, wherein $n=11-20$ and M is selected from the group consisting of:

MgX,
MgR'',
BR₂,
AlR'₂, and
(Ar₂)Zr(X), wherein X is Cl, Br or I, each R is independently a $C_1$ to $C_{10}$ carbon radical with the provision that at least one R group is selected from the group consisting of secondary and tertiary alkyl groups, and each R can be connected to the other as part of a ring structure; R' is a $C_1$ to $C_{20}$ carbon radical, including a 9-alkenyl radical having the empirical formula $C_nH_{2n-1}$; R'' is a $C_2$ to $C_{20}$ carbon radical; and Ar is an aromatic ligand having 5 to 10 carbon atoms.

The 1-metallo-9-alkene prepared as described above is then contacted with oxygen under conditions suitable to form a 9-alkenyl-1-oxymetallo compound as can readily be determined by one skilled in the art. Generally a reaction temperature within the range of room temperature to about $100°$ C. is employed, with a temperature in the range of about $25°-60°$ C. preferred.

Any suitable source of oxygen can be employed, such as for example, air, oxygen-enriched air, pure oxygen, etc. The flow rate of oxygen introduced into the reaction mixture containing the 9-alkenyl-1-metallo compound will be varied as required to maintain the desired reaction temperature during the oxidation step.

Optionally, various metal compound promoters, such as for example, copper, zinc and the like compounds can be added during the oxidation step to aid carrying the reaction to completion.

The 9-alkenyl-1-oxymetallo compound prepared as described above has the empirical formula $C_nH_{2n-1}OM$, wherein $n=11-20$ and M is selected from the group consisting of:

MgX,
MgR'',
BR₂,
AlR'₂, and
(Ar₂)Zr(X), wherein X is Cl, Br or I, each R is independently a $C_1$ to $C_{10}$ carbon radical with the provision that at least one R group is selected from the group consisting of secondary and tertiary alkyl groups, and each R can be connected to the other as part of a ring structure; R' is a $C_1$ to $C_{20}$ carbon radical, including a 9-alkenyl radical having the empirical formula $C_nH_{2n-1}$; R'' is a $C_2$ to $C_{20}$ carbon radical; and Ar is an aromatic ligand having 5 to 10 carbon atoms.

As the final step in the synthetic process of the present invention, the 9-alkenyl-1-oxymetallo compound prepared as described above need only be converted to the desired ester, either by direct esterification of the oxymetallo compound as described in greater detail below, or by esterification employing techniques well known to those of skill in the art.

Preferably, to minimize the number of reaction steps, the 9-alkenyl-1-oxymetallo compound will be converted directly to the desired ester by contact with an esterifying agent, i.e., a $C_1$-$C_{10}$ carboxylic acid or derivative thereof, such as for example, a carboxylic acid anhydride (e.g., acetic anhydride) or a carboxylic acid halide (e.g., acetyl chloride, preferably employing pyridine as an HCl sink). Such direct conversion can be carried out at temperatures in the range of about room temperature up to about $150°$ C.

Note that three of the conversion steps required for the inventive synthetic process can all be done in one reaction pot as a sequential, one-pot conversion. Thus, the 1,9-alkadiene can first be metallated, then oxygenated, and finally esterified, without the need to isolate and purify reaction intermediates along the way.

If desired, the 9-alkenyl-1-oxymetallo compound can be hydrolyzed to produce a 9-alkenyl-1-ol which can then be esterified by conventional methods, or oxidized to produce the aldehyde, if desired.

A further understanding of the present invention and its advantages will be provided by reference to the following nonlimiting examples.

EXAMPLE I

Preparation of 1,9-alkadienes a. Disproportionation catalyst preparation

Disproportionation catalysts were prepared by pouring an aqueous solution of a catalyst precursor over a quantity of catalyst support contained in a beaker fastened to a rotating table. The solution was added at a rate that permitted good absorption of the solution by the silica support.

Thus, the catalyst employed for the following runs was prepared by pouring 26 mL of a solution containing 2.6g of ammonium molybdate (13 mmol) and 0.05g of potassium hydroxide (0.9 mmol) over 20 grams of a high surface area silica support. Once all the support-treating solution had been added to the support, the treated support was first oven dried at about $120°$ C. for 1 hour, then heated in air to about $350°$ C. for about 3 hours.

Catalyst was then loaded into a vertical pipe reactor (½ inch diameter by 20 inches in length) mixed with α-alumina as an inert diluent (5 grams of each). The catalyst was then air oxidized for 6 hours at $450°$ C., then CO treated at $450°$ and 125 psig for about ½ hour, and finally cooled to the desired reaction temperature of about $140°$ C. and a reaction pressure of about 200 psig.

b. 1-Butene disproportionation

A mixture of 660g of cyclooctene (6 mol) and 896g of 1-butene (16 mol) was passed through a guard bed of about ⅓ 3A molecular sieves, ⅓ 13X molecular sieves and ⅓ α-alumina. The pretreated feed was then introduced at the rate of about 4 mL/min to the catalyst bed prepared as described above (maintained at a reaction temperature of about $140°$ C. and a reaction pressure of about 200 psig).

The yield of the desired 1,9-dodecadiene was about 10%.

c. 1-Hexene disproportionation

A mixture of 660g of cyclooctene (6 mol) and 1344g of 1-hexene (16 mol) was subjected to the same pretreatment and reaction conditions as described in part (b)

above. The yield of the desired 1,9-tetradecadiene was within the range of about 5-9%, depending on the length of time the disproportionation reaction had been on stream.

EXAMPLE II preparation of 9-Dodecenyl Acetate a. One-pot conversion of 1,9-dodecadiene

A 12 liter, 3-necked flask equipped with a mechanical stirrer, addition funnel and reflux condenser was charged with 1000g (6 mol) of 1,9-dodecadiene. Diisobutylaluminum hydride (364 mL, 291g, 4.8M in heptane or 2 mol) was added to the diene dropwise over about ½ hour, then the mixture was heated to 110° C. and maintained at that temperature for about 2 hours.

After the diene-aluminum compounds had been heated, the reaction mixture was cooled to room temperature, and oxygen bubbled in to the reaction mixture. After oxygen bubbling had proceeded for about 0.5 hour, 2.3g of cupric chloride was added, then oxygen introduction continued for another 3 hours.

The oxygenated reaction mixture was purged with argon for about 0.75 of an hour, then the mixture was diluted by adding about 500 mL of heptane and 1 liter of tetrahydrofuran (THF). The diluted reaction mixture was warmed to about 80° C., then 868 mL (939g or 9.2 mol) of acetic anhydride was introduced dropwise over about 0.5 hours. The reaction mixture was maintained at 80° C. for about 3 hours before being cooled to about 50° C. for workup.

Product recovery was accomplished by adding about 1 liter of about 3M HCl solution to the organic reaction mixture, the layers separated, and the organic layer washed with 2 liters of saturated sodium bicarbonate solution. The organic layer was separated, dried, then concentrated on the rotary evaporator at reduced pressure. Vacuum distillation gave a 65% yield of 9-dodecenyl acetate, based on the amount of starting diene.

Repetitive runs of this reaction following the above-described procedure have consistently given product yields in the range of 60-70%.

b. Sequential conversion of 1,9-dodecadiene

In a round-bottom flask equipped as described in part (a) of this example, 2013 mL of a 4.8M solution of diisobutylaluminum hydride in heptane (9.66 mol) and 1600g of 1,9-dodecadiene (9.62 mol) were mixed and heated to 100° C. for 4 hours. The reaction mixture was cooled to room temperature, 13g of cupric chloride added, and oxygen bubbled through the solution, with temperature maintained between about 45°-55° C. during oxygen introduction.

After about 4.5 hours of oxygen introduction, product was recovered by adding about 1 liter of 4.4M aqueous HCl, then extracting twice with 1 liter aliquots of hexane. The organic extract was washed with about 1 liter of saturated bicarbonate solution, then solvent removed, giving about a 90% yield of 9-alkenyl-1-ol, as determined by GLC.

About 1500g of 9-alkenyl-1-ol (8 mol) prepared as described in the preceding paragraphs were mixed with 1253g (12.3 mol) of acetic anhydride. Once the initial mixing was complete, 1941g (20.4 mol) of pyridine was added. Cooling was provided to moderate the rate at which the temperature in the reaction vessel rose. Thus, the temperature of the reaction mixture was allowed to rise to 42° C. within about 20 minutes after pyridine introduction, and up to about 52° C. about 30 minutes thereafter.

After the reaction mixture had been stirred for about three hours, product was recovered as follows. The reaction mixture was poured into about 5 liters of 4.4M aqueous HCl, then extracted twice with 2 liter aliquots of hexane. The organic extract was washed with about 2 liters of saturated sodium bicarbonate, dried over $MgSO_4$, filtered and concentrated on the rotary evaporator. The concentrated reaction product was then subjected to fractional distillation at about 0.5 mm Hg pressure. Essentially quantitative yield of 9-dodecenyl acetate was obtained.

EXAMPLE III

Preparation of 9-Tetradecenylacetate 1,9-Tetradecadiene (10g, 0.05 mol) and diisobutylaluminum hydride (57 mL of 1 M solution in hexane; 0.057 mol) were mixed in a round bottom flask, then heated to about 65° C. in an inert atmosphere for about 3 hours. After cooling to room temperature, cupric chloride (0.035g, 0.3 mmol) was added and oxygen bubbled through the reaction mixture for about 3 hours. Temperature was controlled so as not to exceed about 50° C.

When oxygen addition was stopped, the reaction mixture was cooled to room temperature, then 25 mL of acetyl chloride (27.6 g; 0.35 mol) added. The reaction mixture was warmed to about 45° C. for 1.5 hours, then product was recovered by pouring the reaction mixture into 100 mL of 4.4 M aqueous HCl, then extracting with 100 mL of hexane. The organic extract was washed with 100 mL of saturated sodium bicarbonate, dried over $MgSO_4$, concentrated on the rotary evaporator, and finally analyzed by gas liquid chromatography (GLC), which indicated an overall yield of 9-tetradecenyl acetate of about 60% (based on the starting diene).

EXAMPLE IV

Preparation of 9-Tetradecenyl Formate 1,9-Tetradecadiene (10g, 0.05 mol) and diisobutylaluminum hydride (113 mL of 4.8 M solution in heptane; 0.05 mol) were mixed in a round bottom flask, heated to about 100° C. in an inert atmosphere for about three hours, then cooled to room temperature. Cupric chloride (0.07g; 0.5 mmol) was added to the cooled reaction mixture, then oxygen bubbled through the reaction mixture for about three hours, with the temperature controlled so as not to exceed 50° C.

When oxygen addition was stopped, the reaction mixture was cooled to room temperature, and 3.8g (0.05 mol) of ethyl formate was added. The reaction mixture was warmed to about 40° C. and stirred for three hours, then another aliquot of 3.8g of ethyl formate was added, stirred for an additional 0.5 hours, then another aliquot (9.2g, 0.12 mol) of ethyl formate was added. One hour after the final aliquot of ethyl formate was added, a 1 mL sample was removed from the reaction vessel, added to 10 mL of 4.4 M aqueous HCl, extracted with hexane, the organic extract washed with saturated sodium bicarbonate solution, dried over $MgSO_4$, concentrated on the rotary evaporator, and finally analyzed by GLC, which indicated a yield of 81% 9-tetradecenyl formate.

The examples have been provided merely to illustrate the practice of our invention and should not be read so as to limit the scope of our invention or the appended

13 claims in any way. Reasonable variations and modifications, not departing from the essence and spirit of our invention, are contemplated to be within the scope of patent protection desired and sought.

That which is claimed:

1. A process for the synthesis of 9-alkenyl esters which comprises:
  (a) disproportionating cyclooctene and an α-olefin having in the range of 3 up to 12 carbon atoms in the presence of a disproportionation catalyst at a temperature in the range of −20° to 650° C. to produce a 1,9-alkadiene;
  (b) metallating the 1,9-alkadiene obtained in step (a) with a metallating agent under conditions suitable to form a 1-metallo-9-alkene;
  (c) contacting the 1-metallo-9-alkene with oxygen under conditions suitable to form a 9-alkenyl-1-oxymetallo compound; and
  (d) esterifying the 9-alkenyl-1-oxymetallo compound with an esterifying agent to produce the desired 9-alkenyl ester.

2. A process in accordance with claim 1 wherein said disproportionation catalyst is selected from the group consisting of:
  (1) silica or thoria promoted by an oxide or compound convertible to an oxide by calcination, or sulfide of tungsten or molybdenum; or by an oxide or compound convertible to an oxide by calcination of rhenium or tellurium;
  (2) alumina promoted with an oxide or compound convertible to an oxide by calcination of molybdenum, tungsten, or rhenium; a sulfide of tungsten or molybdenum; or an alkali metal salt, ammonium salt, alkaline earth metal salt, or bismuth salt of phosphomolybdic acid;
  (3) one or more of the group aluminum phosphate, zirconium phosphate, calcium phosphate, magnesium phosphate, or titanium phosphate promoted by one or more of a sulfide of molybdenum or tungsten, or an oxide or compound convertible to an oxide by calcination of molybdenum, tungsten or rhenium or magnesium tungstate or beryllium phosphotungstate;
  (4) silica, alumina, aluminum phosphate, zirconium phosphate, calcium phosphate, magnesium phosphate, or titanium phosphate promoted by a hexacarbonyl of molybdenum or tungsten; and
  (5) (a) molybdenum oxide or tungsten oxide associated with suitable support material and (b) at least one organoaluminum compound, optionally, treated with nitric oxide or nitrosyl halides; and
  wherein said disproportionation is carried out at a temperature in the range of 90° to 600° C. for catalyst of group (1), 65° to 260° C. for catalyst of group (2), 315° to 650° C. for catalyst of group (3) −20° to 315° C. for catalyst of group (4), and 0° to 130° C. for catalyst of group (5).

3. A process in accordance with claim 2 wherein said disproportionation catalyst is molybdenum oxide on silica.

4. A process in accordance with claim 1 wherein said metallating agent is a compound selected from the group consisting of:
$R_2BH$,
$AlR'_3$,
$R''MgX$,
$R''_2Mg$, and
$(Ar)_2Zr(X)H$

14 wherein each R is independently a $C_1$ to $C_{10}$ carbon radical wherein at least one R group is selected from the group consisting of secondary and tertiary alkyl groups, and each R. group can be connected to the other as part of a ring structure; wherein each R' is independently H or a $C_1$ to $C_{20}$ carbon radical; R" is a $C_2$ to $C_{10}$ carbon radical; wherein Ar is a cyclopentadienyl compound substituted with about 0 to 5 methyl groups; and wherein X is Cl, Br or I.

5. A process in accordance with claim 1 wherein said metallating agent is
$AlR'_3$
wherein R' is as defined above.

6. A process in accordance with claim 5 wherein $AlR'_3$ is diisobutylaluminum hydride.

7. A process in accordance with claim 1 wherein said α-olefin is 1-butene.

8. A process in accordance with claim 1 wherein said α-olefin is 1-hexene.

9. A process in accordance with claim 1 wherein said esterifying agent is a $C_1$–$C_{10}$ carboxylic acid or derivative thereof.

10. A process in accordance with claim 1 wherein said 9-alkenyl-1-oxymetallo compound is hydrolyzed to the corresponding 9-alkenyl-1-ol, and said 9-alkenyl-1-ol is esterified to produce the desired 9-alkenyl ester.

11. A 1-metallo-9-alkene having the empirical formula $C_nH_{2n-i}M$, wherein $n = 11-20$, wherein M is selected from the group consisting of MgX, MgR", $Br_2$, $AlR'_2$, and $(Ar)_2Zr(X)$, wherein X is Cl, Br or I, each R is independently a $C_1$ to $C_{10}$ carbon radical wherein at least one R group is selected from the group consisting of secondary and tertiary alkyl groups, and each R can be connected to the other as part of a ring structure; each R' is independently H or a $C_1$ to $C_{20}$ carbon radical; R" is a $C_2$ to $C_{10}$ carbon radical; and Ar is a cyclopentadienyl compound substituted with about 0 to 5 methyl groups.

12. A composition in accordance with claim 11 wherein $n=14$ and M is $AlR'_2$.

13. A composition in accordance with claim 11 wherein $n=12$ and M is $AlR'_2$.

14. A 9-alkenyl-1-oxymetallo having the empirical formula $C_nH_{2n-i}OM$ wherein $n=11-20$, wherein M is selected from the group consisting of MgX, MgR", $BR_2$, $AlR'_2$, and $(Ar)_2Zr(X)$, wherein X is Cl, Br or I, each R is independently a $C_1$ to $C_{10}$ carbon radical wherein at least one R group is selected from the group consisting of secondary and tertiary alkyl groups, and each R can be connected to the other as part of a ring structure; each R' is independently H or a $C_1$ to $C_{20}$ carbon radical; R" is a $C_2$ to $C_{10}$ carbon radical; and Ar is a cyclopentadienyl compound substituted with about 0 to 5 methyl groups.

15. A composition in accordance with claim 14 wherein $n=14$ and M is $AlR'_2$.

16. A composition in accordance with claim 14 wherein $n=12$ and M is $AlR'_2$.

17. A process for the synthesis of 9-alkenyl esters which comprises:
  (a) disproportionating cyclooctene and an α-olefin having 3 to 12 carbon atoms in the presence of a disproportionating catalyst comprising molybdenum oxide on silica under disproportionation conditions suitable to produce a 1,9-alkadiene, said conditions including a temperature in the range of 40°–100° C., pressure in the range of 50–1200 psig, for a period of time in the range of 0.5–18 hours;
(b) metallating the 1,9-alkadiene obtained in step (a) with a metallating agent under conditions suitable to form a 1-metallo-9-alkene;
(c) contacting the 1-metallo-9-alkene with oxygen under conditions suitable to form a 9-alkenyl-1-oxymetallo compound; and
(d) esterifying the 9-alkenyl-1-oxymetallo compound with an esterifying agent to produce the desired 9-alkenyl ester.

18. A 1-metallo-9-alkene having the empirical formula $C_nH_{2n-l}M$, wherein $n=11-20$, wherein M is selected from the group consisting of $AlR'_2$ wherein each R' is a 9-alkenyl moiety having the empirical formula $C_{14}H_{27}$.

19. A 1-metallo-9-alkene having the empirical formula $C_nH_{2n-l}M$ wherein $N=11-20$, wherein M is selected from the group consisting of $AlR'_2$ wherein each R' is a 9-alkenyl moiety having the empirical formula $C_{12}H_{23}$.

20. A 9-alkenyl-1-oxymetallo compound having the empirical formula $C_nH_{2n-l}OM$ wherein $n=11-20$, wherein M is selected from the group consisting of $AlR'_2$ wherein each R' is a 9-alkenyl moiety having the empirical formula $C_{14}H_{27}$.

21. A 9-alkenyl-1-oxymetallo compound having the empirical formula $C_nH_{2n-l}OM$ wherein $n=11-20$, wherein M is selected from the group consisting of $AlR'_2$ wherein each R' is a 9-alkenyl moiety having the empirical formula $C_{12}H_{23}$.

* * * * *